US008642976B2

(12) United States Patent
Nakada et al.

(10) Patent No.: US 8,642,976 B2
(45) Date of Patent: Feb. 4, 2014

(54) FLUORESCENCE DETECTING DEVICE AND FLUORESCENCE DETECTING METHOD (75) Inventors: Shigeyuki Nakada, Tamano (JP); Kyouji Doi, Tamano (JP)

(73) Assignee: Mitsui Engineering & Shipbuilding Co., Ltd., Tokyo (JP)

( * ) Notice: Subject to any disclaimer, the term of this patent is extended or adjusted under 35 U.S.C. 154(b) by 237 days.

(21) Appl. No.: 13/148,235

(22) PCT Filed: Feb. 8, 2010

(86) PCT No.: PCT/JP2010/000739
§ 371 (c)(1),
(2), (4) Date: Aug. 5, 2011

(87) PCT Pub. No.: WO2010/092784
PCT Pub. Date: Aug. 19, 2010

(65) Prior Publication Data
US 2011/0284770 A1 Nov. 24, 2011

(30) Foreign Application Priority Data

Feb. 13, 2009 (JP) .................................. 2009-032050

(51) Int. Cl.
*G01J 1/58* (2006.01)
(52) U.S. Cl.
USPC ..................................... 250/458.1; 250/459.1
(58) Field of Classification Search
USPC ........................................... 250/458.1, 459.1
See application file for complete search history.

(56) References Cited

U.S. PATENT DOCUMENTS

| 4,716,363 | A | 12/1987 | Dukes et al. |
| 5,879,900 | A | 3/1999 | Kim et al. |
| 2003/0099574 | A1 | 5/2003 | Bentsen et al. |
| 2009/0283699 | A1 | 11/2009 | Baltz et al. |

FOREIGN PATENT DOCUMENTS

| EP | 1 063 501 A1 | 12/2000 |
| JP | 2645270 B2 | 5/1997 |
| JP | 2000-501838 A | 2/2000 |
| JP | 2001-59811 A | 3/2001 |
| JP | 2005-501256 A | 1/2005 |
| JP | 2006-226698 A | 8/2006 |
| JP | 2007-512504 A | 5/2007 |
| JP | 2007-240424 A | 9/2007 |

*Primary Examiner* — David Porta
*Assistant Examiner* — Abra Fein
(74) *Attorney, Agent, or Firm* — Global IP Counselors, LLP (57) ABSTRACT A fluorescence detecting device generates a modulation signal for modulating an intensity of laser light and modulates the laser light by using the modulation signal, when receiving fluorescence emitted by a measurement object irradiated with laser light emitted from a laser light source unit. The fluorescence detecting device obtains a fluorescent signal of the fluorescence emitted by the measurement object irradiated with the laser light and calculates, from the fluorescent signal, the phase delay of the fluorescence with respect to the modulation signal. At the time, the fluorescence detecting device controls the frequency of the modulation signal so that the value of the phase delay comes close to a preset value. The fluorescence detecting device calculates the fluorescence relaxation time of the fluorescence emitted by the measurement object by using a phase delay obtained under the condition of frequency of the modulation signal at the time when the control is settled.

10 Claims, 6 Drawing Sheets

FLUORESCENCE DETECTING DEVICE AND FLUORESCENCE DETECTING METHOD

TECHNICAL FIELD

The present invention relates to a device and a method for detecting fluorescence by processing a fluorescent signal obtained by receiving fluorescence emitted by a measurement object irradiated with laser light.

BACKGROUND ART

A flow cytometer for use in medical and biological fields includes a fluorescence detecting device that receives fluorescence emitted by a fluorochrome in a measurement object irradiated with laser light and identifies the kind of the measurement object.

More specifically, in the flow cytometer, a suspension liquid containing a measurement object such as a biological material (e.g., cells, DNA, RNA, enzymes, or proteins) labeled with a fluorescent reagent is allowed to flow through a tube together with a sheath liquid flowing under pressure at a speed of about 10 m/sec or less to form a laminar sheath flow. The flow cytometer receives fluorescence emitted by a fluorochrome attached to the measurement object by irradiating the measurement object in the laminar sheath flow with laser light and identifies the measurement object by using the fluorescence as a label.

The flow cytometer can measure, for example, the relative amounts of DNA, RNA, enzymes, proteins, etc. contained in a cell and can quickly analyze their functions. Further, a cell sorter or the like is used to identify a predetermined type of cell or chromosome based on fluorescence and selectively and quickly collect only the identified cells or chromosomes alive.

The use of such a cell sorter is required to quickly and accurately identify more kinds of measurement objects from information about fluorescence.

Patent Document 1 discloses a fluorescence detecting device and a fluorescence detecting method which are capable of accurately and quickly identifying many kinds of measurement objects by calculating the fluorescence lifetime (fluorescence relaxation time) of fluorescence emitted by a measurement object irradiated with laser light.

Patent Document 1 describes that a fluorescence relaxation time is calculated from the phase delay of a fluorescent signal of fluorescence emitted by a measurement object irradiated with intensity-modulated laser light with respect to a modulation signal used for modulating the intensity of laser light.

PRIOR ART DOCUMENT

Patent Document

Patent Document 1: Japanese Patent Application Laid-Open No. 2006-226698

SUMMARY OF INVENTION

Technical Problem

The device and method disclosed in Patent Document 1 are capable of accurately and quickly determining a fluorescence relaxation time, but the range of a fluorescence relaxation time that can be determined with a given accuracy (the range of values of a fluorescence relaxation time) is limited. This results from that the contribution of a phase delay to a fluorescence relaxation time is not constant but is nonlinearly changed. That is, the calculation accuracy of a fluorescence relaxation time widely varies depending on the value of a phase delay. Further, there is also a case where a phase delay varies due to, for example, variable errors caused by constituent devices of the fluorescence detecting device so that a fluorescence relaxation time widely varies. For this reason, the device and method disclosed in Patent Document 1 have a problem in that a fluorescence relaxation time cannot be calculated with a given accuracy.

In order to solve the above problem, it is an object of the present invention to provide a fluorescence detecting device and a fluorescence detecting method which can accurately calculate a fluorescence relaxation time with a given accuracy over a wide range.

Solution to Problem

According to an aspect of the invention, there is provided a device for detecting fluorescence by processing a fluorescent signal obtained by receiving fluorescence emitted by a measurement object which is irradiated with laser light.

The device includes:

a light source unit operable to emit laser light with which a measurement object is irradiated while modulating an intensity of the laser light;

a light-receiving unit operable to output a fluorescent signal of fluorescence emitted by the measurement object irradiated with the laser light;

a light source control unit operable to generate a modulation signal for modulating the intensity of the laser light emitted from the light source unit;

a processing unit operable to calculate, from the fluorescent signal output by the light-receiving unit, a phase delay of the fluorescence emitted by the measurement object with respect to the modulation signal and calculates a fluorescence relaxation time of the fluorescence of the measurement object using the phase delay; and a signal control unit operable to control a frequency of the modulation signal so that a value of the phase delay comes close to a preset value.

According to another aspect of the invention, there is provided a method for detecting fluorescence by processing a fluorescent signal obtained by receiving fluorescence emitted by a measurement object which is irradiated with laser light.

The method includes the steps of:

generating a modulation signal for modulating an intensity of laser light emitted from a laser light source unit to modulate the laser light by using the modulation signal;

obtaining a fluorescent signal of fluorescence emitted from a measurement object irradiated with the laser light;

calculating, from the fluorescent signal, a phase delay of the fluorescence with respect to the modulation signal;

controlling a frequency of the modulation signal so that a value of the phase delay comes close to a preset value; and calculating a fluorescence relaxation time of the fluorescence emitted by the measurement object by using the phase delay obtained under a condition of the frequency of the modulation signal at a time when the control of the frequency is settled.

Advantageous Effects of the Invention

The fluorescence detecting device and fluorescence detecting method according to the present invention calculates a fluorescence relaxation time by adjusting the frequency of a modulation signal for modulating the intensity of laser light so that a phase delay comes close to a preset value, thereby making the contribution of a phase delay to a fluorescence relaxation time not nonlinear but constant. This makes it possible to expand the range of a fluorescence relaxation time that can be calculated with a given accuracy. For example, when fluorescence is a relaxation response of a first-order lag, tan θ (θ is defined as the phase delay), which is a nonlinear part, is allowed to have a substantially constant value irrespective of a fluorescence relaxation time. This makes it possible to prevent the calculation accuracy of a fluorescence relaxation time from varying due to a great difference in the contribution of tan θ between when the phase delay θ is large and when the phase delay θ is small.

Particularly, by setting the preset value to 45 degrees, the sensitivity of the phase delay to be calculated to the frequency of the modulation signal can be made high, thereby calculating a fluorescence relaxation time with high accuracy.

DESCRIPTION OF EMBODIMENTS

Hereinbelow, the present invention will be described in detail based on a flow cytometer appropriately using a fluorescence detecting device according to the present invention.

Figure 1:
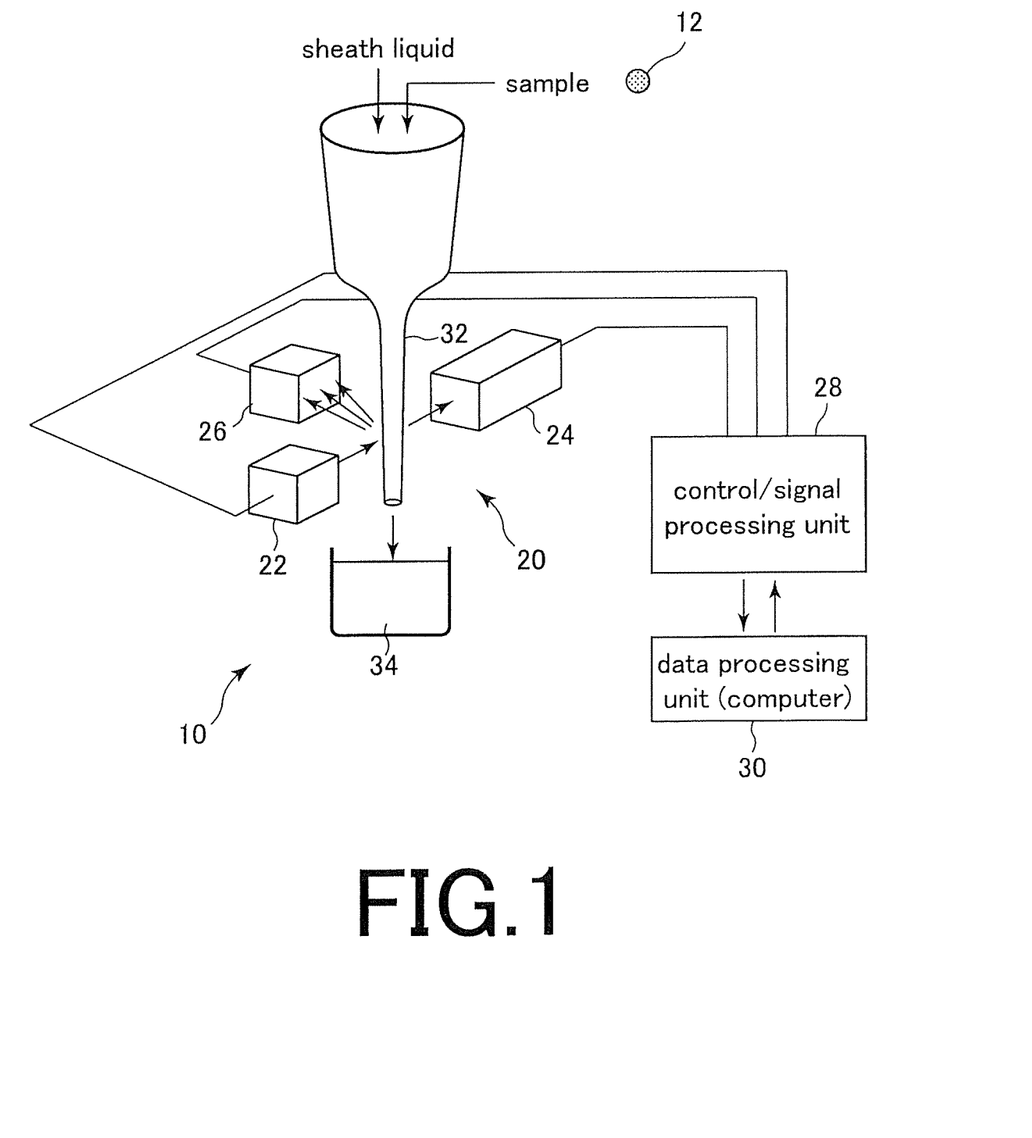
FIG. 1 is a schematic diagram illustrating the structure of a flow cytometer using a fluorescence detecting device according to the present invention.
Figure 2:
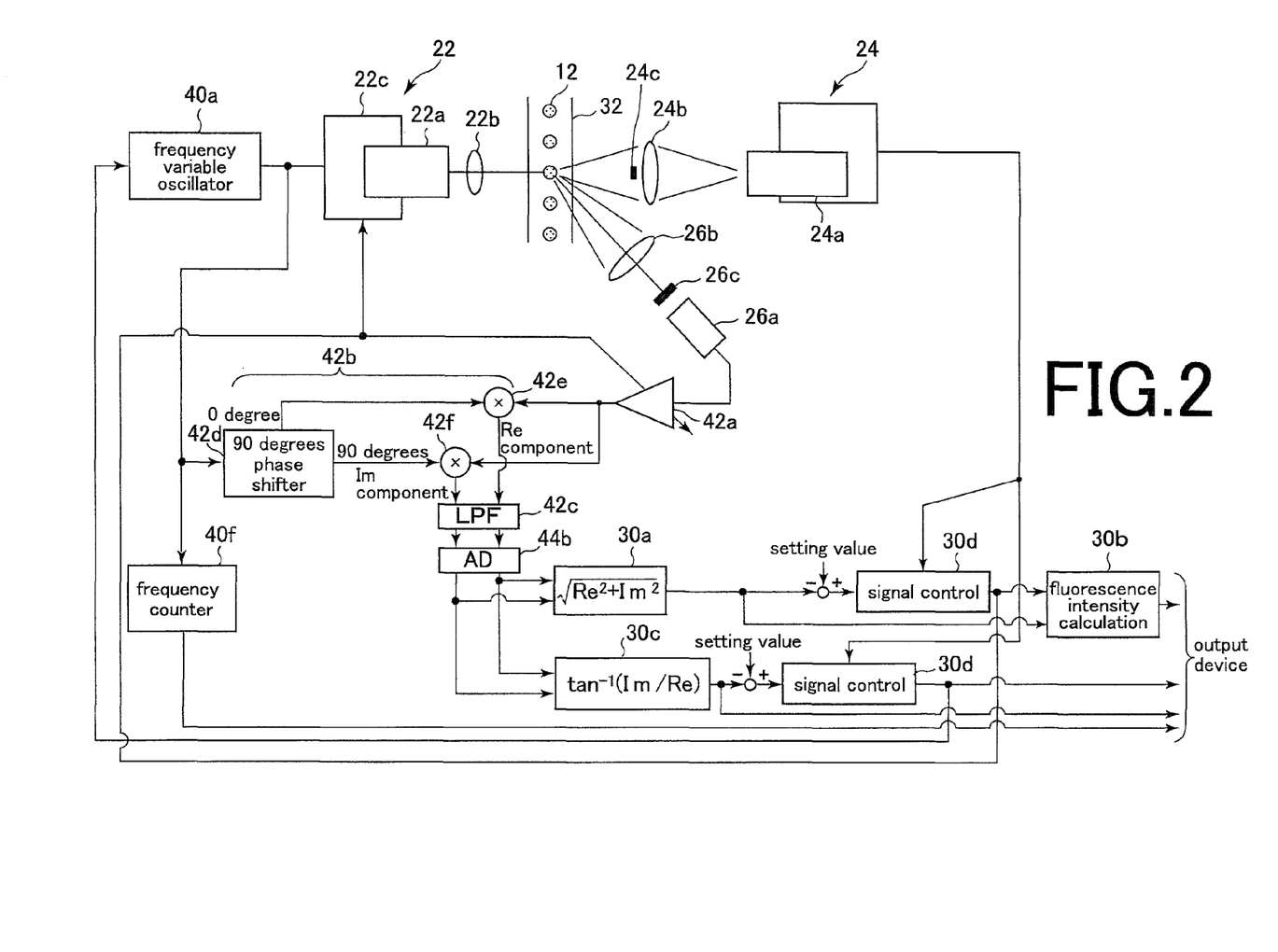
FIG. 2 is a diagram mainly illustrating the flow of signals in the flow cytometer illustrated in FIG. 1.

FIG. 1 is a schematic diagram illustrating the structure of a flow cytometer 10 using the fluorescence detecting device according to the present invention. FIG. 2 is a diagram mainly illustrating the flow of signals in the flow cytometer 10.

The flow cytometer 10 mainly includes a laser light source unit 22, light-receiving units 24 and 26, a control/signal processing unit 28, a data processing unit (computer) 30, a tube 32, and a collection vessel 34.

The laser light source unit 22 emits laser light having a wavelength within a visible light band of 350 nm to 800 nm while modulating the intensity of the laser light by a controlled modulation signal. The modulation frequency and signal level of a DC component of the modulation signal are controlled.

The laser light source unit 22 includes a laser light source 22a, a lens system 22b (see FIG. 2), and a laser driver 22c (see FIG. 2). The laser light source 22a emits laser light of a predetermined wavelength as CW (continuous-wave) laser light of constant intensity while frequency-modulating the intensity of the CW laser light. The lens system 22b focuses laser light on a predetermined measurement point (measurement field) in the tube 30. The laser driver 22c drives the laser light source. As described above, the laser light source unit 22 includes one laser light source, but the number of laser light sources employed is not limited to one. The laser light source unit 22 may employs two or more laser light sources. In this case, it is preferred that laser beams emitted from two or more laser light sources are combined together by a dichroic mirror or the like to emit the combined laser beams to the measurement field.

As the laser light source that emits laser light, for example, a semiconductor laser is employed. The laser light has an output of, for example, about 5 to 100 mW. On the other hand, the frequency (modulation frequency) at which the intensity of the laser light is modulated has a periodical cycle time slightly longer than a fluorescence relaxation time, and is, for example, 10 to 200 MHz.

The laser driver 22c provided in the light source unit 22 is configured so as to control the level of the DC component of intensity of laser light and the frequency of intensity modulation. That is, the intensity of laser light makes a change caused by superimposing intensity modulation on the DC component, and the minimum intensity of laser light is larger than 0.

The light receiving unit 24 includes a photoelectric converter 24a (see FIG. 2), a lens system 24b (see FIG. 2), and a shielding plate 24c (see FIG. 2). The lens system 24b focuses forward-scattered light on the photoelectric converter 24a.

The photoelectric converter 24a is arranged so as to be opposed to the laser light source unit 22 with the tube 32 being provided therebetween. The photoelectric converter 24a receives laser light forward-scattered by the sample 12 passing through the measurement field and outputs a detection signal indicating the passage of the sample 12 through the measurement point.

The shielding plate 24c is provided in front of the lens system 24b to prevent laser light from directly entering the photoelectric converter 24a. The signal output from the light-receiving unit 24 is supplied to the control/signal processing unit 28 and the data processing unit 30, and is used in the control/signal processing unit 28 and the data processing unit 30 as a trigger signal to inform the timing of passage of the sample 12 through the measurement point in the tube 32 and as an OFF signal for terminating measurement.

On the other hand, the light-receiving unit 26 is arranged in a direction perpendicular to a direction in which laser light emitted from the laser light source unit 22 travels and to a direction in which the sample 12 moves in the tube 32. The light-receiving unit 26 includes a photoelectric converter 26a (see FIG. 2) that receives fluorescence emitted by the sample 12 irradiated with laser light at the measurement point.

The light-receiving unit 26 further includes, in addition to the photoelectric converter 26a, a lens system 26b (see FIG. 2) and a band-pass filter 26c (see FIG. 2). The lens system 26b focuses a fluorescent signal from the sample 12.

The lens system 26b is configured so as to focus fluorescence received by the light-receiving unit 26 on the light-receiving surface of the photoelectric converter 26a. The band-pass filter 26c has a transmission wavelength band set to perform filtering so that fluorescence of a predetermined wavelength band can be received by the photoelectric converter 26a.

The light-receiving unit 26 has one photoelectric converter 26a, but according to this embodiment, the light-receiving unit 26 may employ two or more photoelectric converters. In this case, the light-receiving unit 26 may have a structure in which a dichroic mirror is provided in front of the band-pass filter 26c to separate fluorescence according to a frequency band and separated beams of the fluorescence are received by the two or more photoelectric converters, respectively.

The band-pass filter 26c is provided in front of the light-receiving surface of each of the photoelectric converters 26a, and transmits only fluorescence of a predetermined wavelength band. The wavelength band of fluorescence that can pass through the band-pass filter 26c is set so as to correspond to the wavelength band of fluorescence emitted by a fluorochrome.

The photoelectric converter 26a is equipped with, for example, a photomultiplier as a sensor. The photoelectric converter 26a converts light received on its photoelectric surface into an electrical signal. Here, fluorescence received by the photoelectric converter is intensity-modulated fluorescence because the fluorescence is emitted by irradiation with intensity-modulated laser light, and therefore an output fluorescent signal has the same frequency as the intensity-modulated laser light. The fluorescent signal is supplied to the control/signal processing unit 28.

Figure 3:
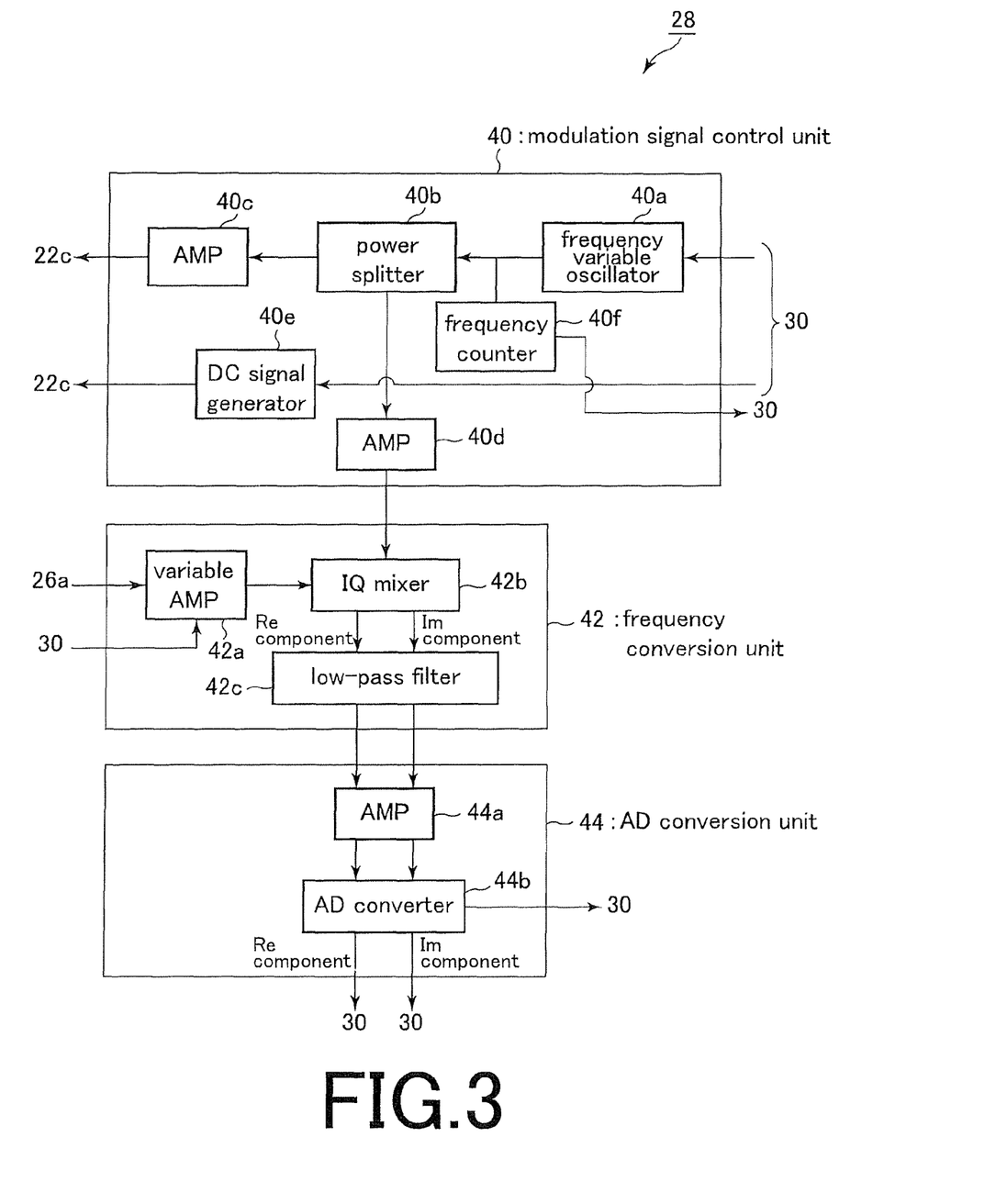
FIG. 3 is a schematic diagram illustrating the structure of a control/signal processing unit of the flow cytometer illustrated in FIG. 1.

FIG. 3 is a diagram illustrating the structure of the control/signal processing unit 28. The control/signal processing unit 28 includes a modulation signal control unit 40, a frequency conversion unit 42, and an AD conversion unit 44.

The modulation signal control unit 40 generates a modulation signal for modulating the intensity of laser light and supplies the modulation signal to the laser driver 22c. Further, the modulation signal control unit 40 supplies the generated modulation signal also to the frequency conversion unit 42.

The modulation signal control unit 40 includes a frequency variable oscillator 40a, a power splitter 40b, amplifiers 40c and 40d, a DC signal generator 40e, and a frequency counter 40f.

The frequency variable oscillator 40a oscillates at a frequency determined according to a control signal supplied from the data processing unit 30 to generate a modulation signal. As the frequency variable oscillator 40a, for example, a voltage-controlled oscillator is preferably used.

The power splitter 40b evenly divides the generated modulation signal, and supplies the split modulation signals to the amplifiers 40c and 40d.

The amplifier 40c amplifies the modulation signal and supplies the amplified modulation signal to the laser driver 22c. The amplifier 40d amplifies the modulation signal and supplies the amplified modulation signal to the frequency conversion unit 42 (which will be described later). The modulation signal supplied to the frequency conversion unit 42 is used as a reference signal to calculate the phase delay of the fluorescent signal output from the light-receiving unit 26 with respect to the modulation signal.

The DC signal generator 40e generates a DC component of the modulation signal and supplies the DC component to the laser driver 22c. The DC component supplied to the laser driver 22c is used to adjust the intensity of laser light so that the intensity of fluorescence emitted by the sample 12 is adjusted to a predetermined level in order to accurately calculate a phase delay value and a fluorescence relaxation time. That is, the DC component is supplied to the laser driver 22c so that the intensity of laser light makes a change caused by superimposing intensity modulation on the DC component and the minimum intensity of laser light becomes larger than 0.

The frequency counter 40f counts the frequency of the modulation signal generated by the frequency variable oscillator 40a. The result of counting by the frequency counter 40f is supplied to the data processing unit 30.

The frequency variable oscillator 40a and the DC signal generator 40e are both connected to the data processing unit 30 so that the frequency of the modulation signal and the signal level of the DC component are controlled by control signals supplied from the data processing unit 30.

The frequency conversion unit 42 performs down conversion by frequency conversion of a fluorescent signal supplied from the light-receiving unit 26a. The frequency conversion unit 42 mainly includes a variable amplifier 42a, an IQ mixer 42b, and a low-pass filter 42c.

The variable amplifier 42a amplifies the fluorescent signal, and is connected to the data processing unit 30 so that its gain is controlled according to a control signal supplied from the data processing unit 30.

The IQ mixer 42b performs frequency-down conversion on the amplified fluorescent signal by using the modulation signal supplied from the modulation signal control unit 40 as a reference signal, and generates the fluorescent signal in phase with the modulation signal and the fluorescent signal which is phase-shifted by 90 degrees with respect to the modulation signal.

The IQ mixer 42b includes a 90 degrees phase shifter 42d (see FIG. 2) and mixers 42e (see FIG. 2) and 42f (see FIG. 2). The 90 degree phase shifter 42d generates a signal whose phase is shifted by 90 degrees with respect to the modulation signal, and supplies the in-phase modulation signal and the 90 degrees phase-shifted modulation signal to the mixer 42e and the mixer 42f, respectively.

The amplified fluorescent signal is mixed, by the mixer 42e, with the in-phase modulation signal supplied as a reference signal, and is then supplied to the low-pass filter 42c. The amplified fluorescent signal is mixed, by the mixer 42f, with the 90 degrees phase-shifted modulation signal supplied as a reference signal, and is then supplied to the low-pass filter 42c.

The low-pass filter 42c performs filtering to extract, as a low-frequency signal, a signal of a predetermined frequency band lower than the frequency of the modulation signal from the fluorescent signal mixed with the modulation signal. As a result, Re and Im components of the fluorescent signal which mainly include a signal component of a zero-frequency band are determined. The determined Re and Im components are supplied to the AD conversion unit 44.

The AD conversion unit 44 converts the supplied Re and Im components into digital data. The AD conversion unit 44 includes an amplifier 44a and an AD converter 44b. The amplifier 44a amplifies the Re and Im components with a predetermined gain, and supplies the amplified Re and Im components to the AD converter 44b. The AD converter 44b converts the amplified Re and Im components into digital data, and supplies the digitized Re component data and the digitized Im component data to the data processing unit 30.

The data processing unit 30 determines the phase delay $\theta$ of fluorescence and the value of a fluorescence intensity signal by using the supplied Re component data and Im component data. Further, the data processing unit 30 calculates, by using the phase delay $\theta$, a fluorescence relaxation time $\tau$ at a time when the value of the phase delay $\theta$ comes close to a preset value and the value of the fluorescence intensity signal falls within a preset intensity range, and calculates the fluorescence intensity of fluorescence at that time.

More specifically, a control signal for adjusting the level of the DC component generated by the DC signal generator 40e or the gain of the variable amplifier 42a is generated until the value of the calculated fluorescence intensity signal falls within a preset intensity range to adjust the signal levels of the Re component and the Im component A/D-converted by the A/D converter 44b. Further, a control signal for adjusting the frequency of the modulation signal generated by the frequency variable oscillator 40a is generated so that the value of the calculated phase delay θ comes close to a preset value to control the modulation signal. As can be seen from the graph illustrated in FIG. 5A which will be described later, the preset value can be set to 25 to 65 degrees at which the change of the value of the phase delay θ with respect to the change of the angular frequency can be made large. Particularly, the preset value is preferably 45 degrees. The phrase "comes close to a preset value" means that the value of the phase delay θ obtained after the control of the modulation signal is closer to a preset value than the value of the phase delay θ obtained before the control of the modulation signal. The value of the phase delay θ comes close to a preset target value by the control, but preferably converges within an acceptable range previously set with respect to the target value. The acceptable range depends on a target calculation accuracy of a fluorescence relaxation time, but is, for example, ±10 degrees, ±5 degrees, or ±2 degrees. When the value of the phase delay θ falls within the acceptable range previously set with respect to the target value, the control is settled.

Figure 4:
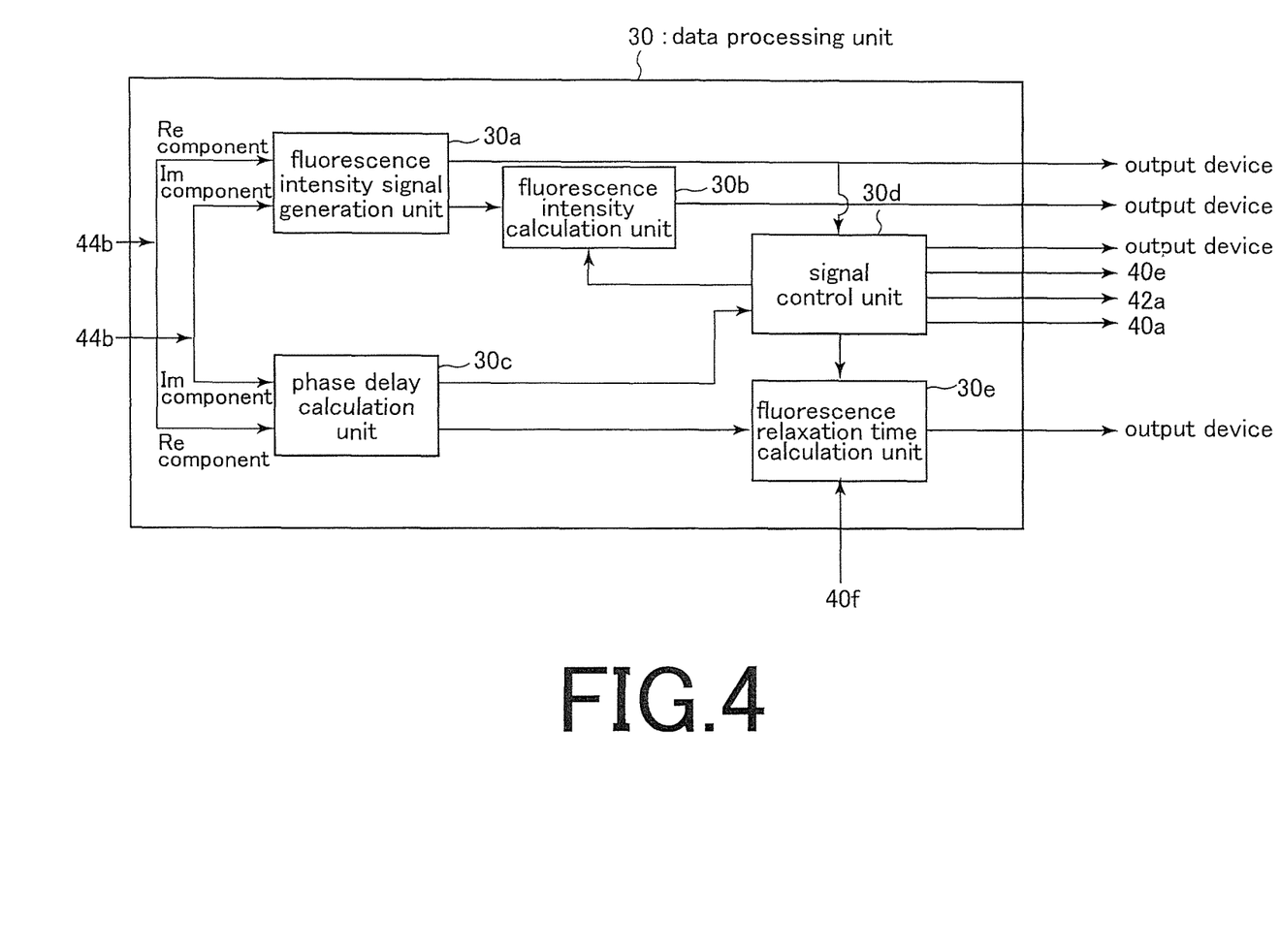
FIG. 4 is a schematic diagram illustrating the structure of a data processing unit of the flow cytometer illustrated in FIG. 1.

FIG. 4 is a schematic diagram illustrating the structure of the data processing unit 30. The data processing unit 30 includes a fluorescence intensity signal generation unit 30*a*, a fluorescence intensity calculation unit 30*b*, a phase delay calculation unit 30*c*, a signal control unit 30*d*, and a fluorescence relaxation time calculation unit 30*e*. These units are modules provided by executing a computer-executable program. That is, the data processing unit 30 performs its function by executing software on the computer.

The phase delay calculation unit 30*c* and the fluorescence relaxation time calculation unit 30*e* correspond to at least a processing unit that calculates, from the fluorescent signal, the phase delay of fluorescence with respect to the modulation signal and calculates the fluorescence relaxation time of fluorescence emitted by the sample 12 by using the calculated phase delay.

The fluorescence intensity signal generation unit 30*a* determines the square route of the addition of the squares of the Re component data and the Im component data supplied from the AD converter 44*b* to generate a fluorescence intensity signal. The calculated fluorescence intensity signal is sent to the fluorescence intensity calculation unit 30*b*. The value of the fluorescence intensity signal is a value obtained as a result of adjusting the DC component of laser light and the gain of the variable amplifier 42*a*, and therefore widely varies according to the result of adjusting them. Therefore, the fluorescence intensity calculation unit 30*b* corrects the fluorescence intensity signal by using information about the level of the DC component of the intensity of laser light and the gain to calculate a fluorescence intensity. However, this correction is not performed until the fluorescence intensity calculation unit 30*b* receives a decision instruction (which will be described later) given by the signal control unit 30*d*.

It is to be noted that the fluorescence intensity signal is time-series data calculated by using the Re component data and the Im component data supplied continuously during the time period when the sample 12 passes through the measurement field irradiated with laser light.

In response to the decision instruction given by the signal control unit 30*d*, the fluorescence intensity calculation unit 30*b* corrects the fluorescence intensity signal generated by the fluorescence intensity signal generation unit 30 by using information about the level of the DC component of the intensity of laser light and the gain to calculate a fluorescence intensity. More specifically, the fluorescence intensity is determined by dividing the value of the fluorescence intensity signal by a coefficient determined from the values of the control signals for adjusting the level of the DC component and the gain of the variable amplifier 42*a*. It is to be noted that the coefficient used for division is obtained by referring to LUT that associates the values of the control signals for adjusting the level of the DC component and the gain with the coefficients.

The DC component of laser light used for correction may be a signal value given by the control signal or the intensity of forward-scattered light measured by the light-receiving unit 24. The gain of the variable amplifier 42*a* may be a signal value given by the control signal or a value obtained by separately measuring the gain.

The decision instruction is given by the signal control unit 30*d* when the value of the fluorescence intensity signal generated during control by the fluorescence intensity signal generation unit 30*a* exceeds a predetermined setting value and reaches its maximum. Here, the predetermined setting value is a lower limit defining the preset range. The fluorescence intensity is obtained by dividing the value of the fluorescence intensity signal at this time by the value of the control signal.

The adjustment of the level of the DC component generated by the DC signal generator 40*e* and the gain of the variable amplifier 42*a* (adjustment of operation amounts) is performed so that the value of the fluorescence intensity signal falls within the preset intensity range, but the fluorescence intensity signal becomes weak in the latter half of the time period during which the sample 12 passes through the measurement field. At this time, the value of the fluorescence intensity signal does not reach its target value by the adjustment of the level of the DC component generated by the DC signal generator 40*e* and the gain of the variable amplifier 42*a* (by the adjustment of operation amounts), even when the operation amounts are maximized. On the other hand, in the stage from the first half to the middle of the time period during which the sample 12 passes through the measurement field, the fluorescence intensity signal becomes gradually strong. Therefore, once the value of the fluorescence intensity signal falls within the preset range in this stage, the operation amounts are not adjusted and become constant. At this time, the value of the fluorescence intensity signal exceeds the setting value defining the preset range and reaches its maximum. Therefore, the value of the fluorescence intensity signal at this time is divided by a coefficient determined from the values of the control signals at this time to determine a corrected fluorescence intensity.

The value of a fluorescence intensity can be calculated through the above method, but may be calculated by integrating values obtained by dividing the value of the fluorescence intensity signal during control by a coefficient determined from the values of the control signals during the time period of control and then by dividing the integrated value by the control time.

The phase delay calculation unit 30*c* calculates the phase delay θ by calculating $\tan^{-1}(\text{Im}/\text{Re})$ (Im is the value of the Im component data and Re is the value of the Re component data) by using the supplied Re component data and Im component data. The calculated phase delay θ is supplied to the signal control unit 30*d* and the fluorescence relaxation time calculation unit 30*e*.

The fluorescence relaxation time calculation unit 30*e* determines, in response to the decision instruction given by the signal control unit 30*d*, the fluorescence relaxation time τ according to the equation, $\tau = 1/(2\pi f) \cdot \tan\theta$ by using the phase delay θ supplied from the phase delay calculation unit 30*c*. The reason why the fluorescence relaxation time τ can be determined according to the above equation is that fluorescence is substantially a relaxation response of a first-order lag. It is to be noted that the frequency f of the modulation signal is the result of counting the frequency of the modulation signal supplied from the frequency counter 40f. Instead of the result of counting the frequency of the modulation signal, the frequency f of the modulation signal may be a target frequency of the modulation signal determined by the control signal supplied from the signal control unit 30.

The signal control unit 30d determines whether the value of the phase delay θ supplied from the phase delay calculation unit 30c and the value of the fluorescence intensity signal generated by the fluorescence intensity signal generation unit 30a fall within their respective preset ranges, and generates a control signal according to the determination result.

More specifically, the signal control unit 30d controls the frequency of the modulation signal so that the value of the phase delay θ comes close to the preset value, for example, 45 degrees. The signal control unit 30d generates a control signal for adjusting the oscillation frequency of the frequency variable oscillator 40a so that the value of the phase delay θ comes close to the preset value, and supplies the control signal to the frequency variable oscillator 40a. This makes it possible to supply the frequency-adjusted modulation signal to the laser driver 22c so that the intensity modulation of laser light is adjusted.

When the value of the phase delay θ corresponds with 45 degrees within the setting acceptable range, the signal control unit 30d determines that the phase delay θ has been obtained with high accuracy according to the determination result of the value of the fluorescence intensity signal (which will be described later).

Further, the signal control unit 30d controls the level of the DC component of laser light emitted from the light source unit 22 and the gain of the variable amplifier 44b so that the value of the fluorescence intensity signal falls within the preset range.

When determining that the value of the fluorescence intensity signal does not fall within the preset range, the signal control unit 30d generates a control signal for adjusting the signal level of the DC component generated by the DC signal generator 40e and supplies the control signal to the DC signal generator 40e. This makes it possible to supply the modulation signal whose signal level of the DC component has been adjusted to the laser driver 22c so that the intensity modulation of laser light is adjusted. This makes it possible to supply the modulation signal whose signal level of the DC component has been adjusted to the laser driver 22c. Further, the signal control unit 30d generates a control signal for adjusting the gain of the variable amplifier 42a provided just behind the light-receiving unit 26a to control the gain of the variable amplifier 42a.

According to this embodiment, the modulation signal of the DC signal generator 40e and the gain of the variable amplifier 26a are controlled, but only the modulation signal may be controlled.

When the value of the phase delay θ falls within the preset range and the value of the fluorescence intensity signal also falls within the preset range, the signal control unit 30d determines that the phase delay θ has been obtained with high accuracy, and gives the decision instruction for calculation of a fluorescence intensity and a fluorescence relaxation time to the fluorescence intensity calculation unit 30b and the fluorescence relaxation time calculation unit 30e.

As described above, when the value of the phase delay θ and the value of the fluorescence intensity signal both fall within their respective preset ranges, the phase delay θ is obtained with high accuracy. Thereby, a fluorescence relaxation time can be calculated with the high accuracy. According to this embodiment, the phase delay θ is obtained with high accuracy by at least determining whether the value of the phase delay θ corresponds with a target value of 45 degrees within the acceptable range.

Figure 5A:
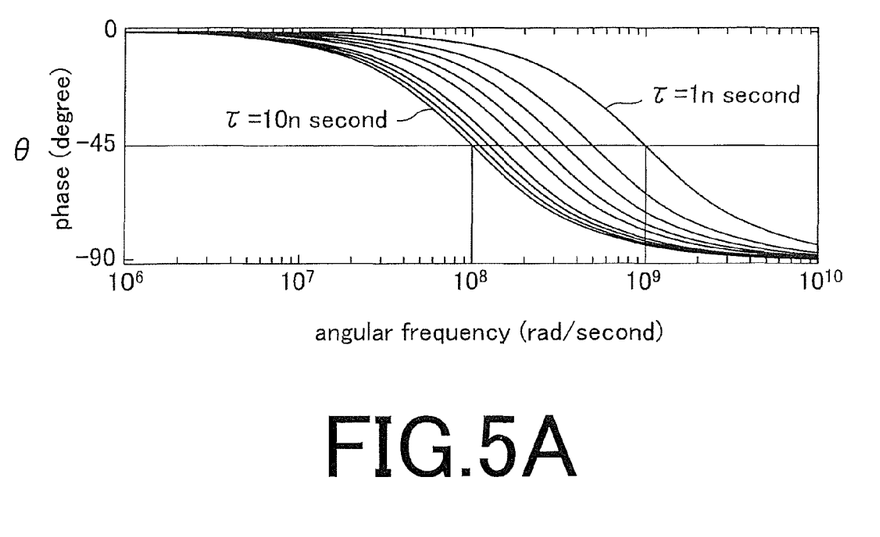
FIGS. 5A and 5B are graphs for explaining the effect of adjustment of a phase delay θ performed in the fluorescence detecting device according to the present invention and in a phase detecting method according to the present invention.

FIG. 5A is a graph illustrating the relationship between the frequency (angular frequency 2πf) at which the intensity of laser light is modulated and the phase delay θ of fluorescence emitted by irradiation with the laser light, which is determined for different values of the fluorescence relaxation time τ.

When the phase delay θ is 45 degrees, the angular change of the phase delay θ with respect to the angular frequency 2πf is maximized. That is, the sensitivity of the phase delay θ is high at an angle of 45 degrees. Therefore, by controlling the frequency of the modulation signal so that the phase delay θ comes close to a target value of 45 degrees, the sensitivity of the phase delay θ to be calculated can be made high. Thereby, the phase delay θ can be obtained with high accuracy.

Figure 5B:
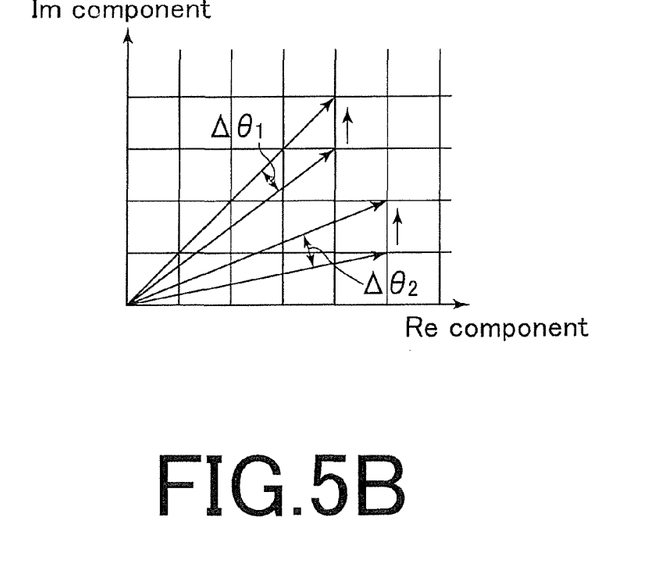

As illustrated in FIG. 5B, even when the Re component or the Im component has an error and therefore the quantization level of AD conversion performed by the AD converter 44b is changed by one, the change $\Delta\theta_1$ of the phase delay at the time when the phase delay θ corresponds with a target value of 45 degrees within the acceptable range is smaller than the change $\Delta\theta_1$ of the phase delay at the time when the phase delay θ falls within a range other than the acceptable range. Therefore, the error of the phase delay θ caused by a quantization error can be reduced when the phase delay θ corresponds with 45 degrees within the acceptable range.

Figure 6:
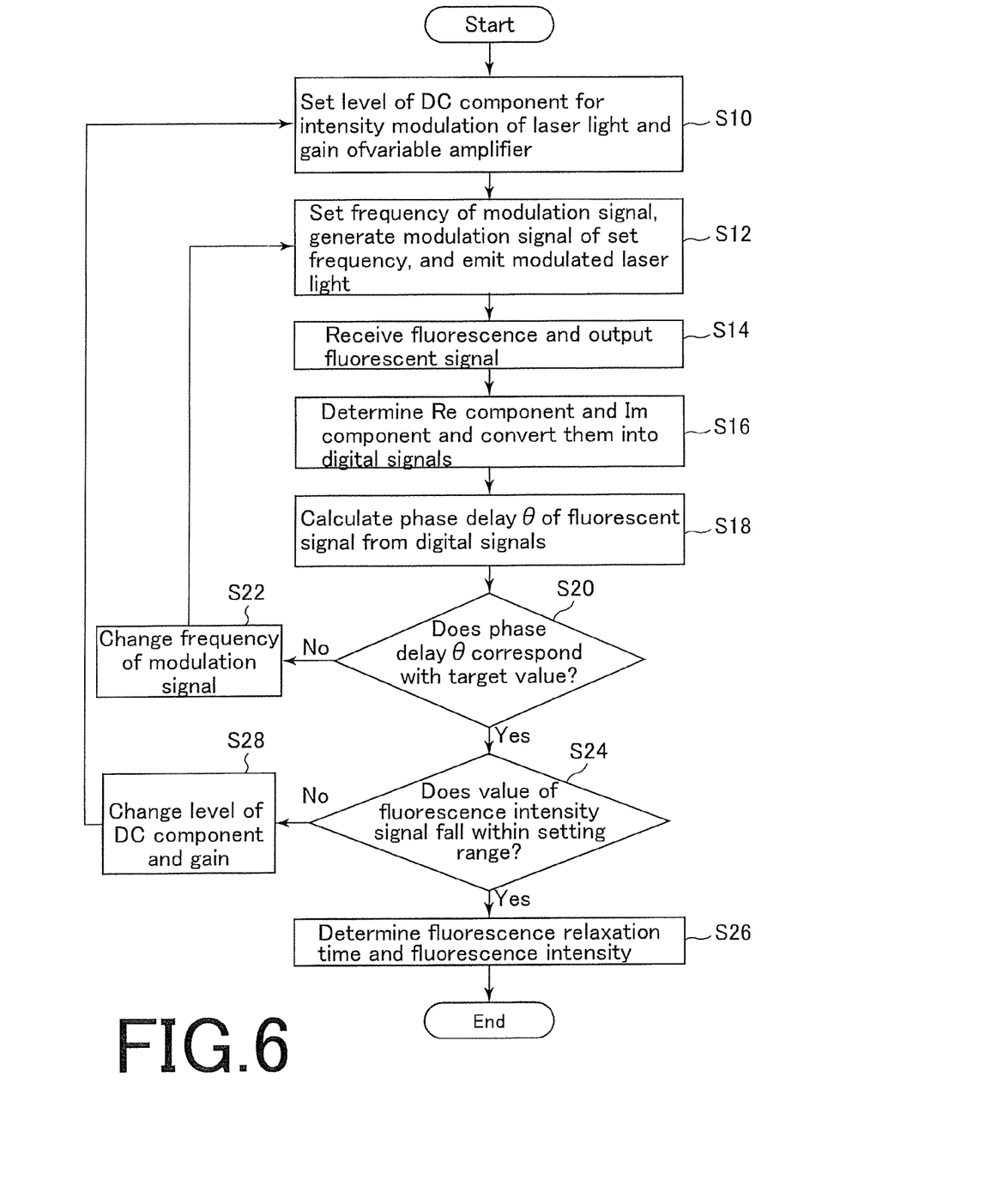
FIG. 6 is a flow chart for explaining one embodiment of the fluorescence detecting method according to the present invention.

FIG. 6 is a flow chart for explaining one embodiment of a fluorescence detecting method using the fluorescence detecting unit 10. According to the method of this embodiment, the DC component of the intensity of laser light, the amplification gain of a fluorescent signal just after receiving fluorescence, and the frequency of a modulation signal are adjusted to calculate a fluorescence intensity and a fluorescence relaxation time.

First, the signal level of the DC component of a modulation signal generated by the modulation signal control unit 40 to modulate the intensity of laser light and the gain of the variable amplifier 42a of the frequency conversion unit 42 are set based on control signals supplied from the data processing unit 30 (Step S10). At the beginning of processing, the signal level of the DC component and the gain are set to default values.

Then, the frequency of the modulation signal is set by the modulation signal control unit 40 based on a control signal supplied from the data processing unit 30. For example, the frequency is set to a default value. A modulation signal is generated using the thus set signal level of the DC component, gain, and frequency of the modulation signal, and intensity-modulated laser light is emitted from the laser light source 22a (Step S12).

Then, fluorescence emitted by the sample 12 passing through the measurement field by irradiation with laser light is received by the light-receiving unit 26a, and a fluorescent signal is output (Step S14).

Then, the fluorescent signal is amplified with the gain set by the variable amplifier 42a, supplied to the mixers 42e and 42f, and mixed with the modulation signal to determine a Re component and an Im component. Further, the Re component and the Im component are converted by the AD converter 44 into digital signals so that Re component data and Im component data are obtained (Step S16).

Then, the phase delay calculation unit 30c of the data processing unit 30 calculates the phase delay θ of the fluorescent signal from the digitized Re component data and Im component data (Step S18).

Then, the signal control unit 30d determines whether the calculated phase delay θ corresponds with a preset target value of 45 degrees within an acceptable range (Step S20). When the phase delay θ does not correspond with the target value within the acceptable range, a control signal for changing the frequency of the modulation signal is generated and supplied to the frequency variable oscillator 40a. As a result, the frequency of the modulation signal is changed (Step S22). Here, the changing of the frequency is performed using the calculated phase delay θ so that the frequency becomes a value calculated by, for example, frequency $f=2\pi f_1/\tan(\theta)$ ($f_1$ is the current frequency of the modulation signal).

A series of Steps S10 to S22 is repeated so that the phase delay θ comes close to the preset target value.

When the result of the determination in Step S20 is YES, the signal control unit 30 further determines whether the value of a fluorescence intensity signal falls within a preset range (Step S24). When the value of the fluorescence intensity signal falls within the preset range (i.e., when the result of the determination is YES), the signal control unit 30 gives a decision instruction for calculation of a fluorescence intensity and a fluorescence relaxation time to the fluorescence intensity calculation unit 30b and the fluorescence relaxation time calculation unit 30e. In this way, the fluorescence intensity calculated by the fluorescence intensity signal generation unit 30a and the fluorescence relaxation time calculated by the fluorescence relaxation time calculation unit 30e are determined as measurement results of the sample 12 (Step S26).

When the value of the fluorescence intensity signal does not fall within the preset range (i.e., when the result of the determination is No), the signal level of the DC component used for the modulation signal and the gain are changed (Step S28), and the processing is returned to Step S10.

In this way, a series of Steps S10 to S24 and S28 is repeated until the value of the fluorescence intensity signal falls within the preset range.

The calculated measurement results are output together with information about the signal level of the DC component, the gain, the frequency of the modulation signal, etc. to an output device (not illustrated) such as a display or a printer.

As described above, the fluorescence detecting method performs a process in which the determination as to whether the phase delay θ corresponds with a target value within an acceptable range is made, and when the determination result is YES, the determination as to whether the value of the fluorescence intensity signal falls within a setting range is made. However, the method according to this embodiment may perform a process in which the determination as to whether the value of the fluorescence intensity signal falls within a setting range is made, and when the determination result is YES, the determination as to whether the phase delay θ corresponds with a target value within an acceptable range is made. Alternatively, the above-described two determinations may be made at the same time.

Such a control of the frequency of the modulation signal using the flow cytometer illustrated in FIG. 1 may be performed in the following manner. Assuming that the sample 12 is composed of a plurality of sample particles and the sample particles pass through the measurement field irradiated with laser light one by one intermittently at a constant rate, the signal control unit 30d begins the control of the frequency of the modulation signal just after the sample particle begins to pass through the measurement field irradiated with laser light so that the value of a phase delay comes close to a preset value. Then, the data processing unit 30 finds the frequency of the modulation signal at which the value of a phase delay becomes equal to the preset value before the sample particle passes over the measurement field irradiated with laser light, and calculates a fluorescence relaxation time from a phase delay obtained under the condition of the found frequency and the frequency of the modulation signal. At the same time, the signal level of the DC component of the modulation signal and the gain of the variable amplifier 42a are also controlled.

It takes about 10 to 30 μsec for the sample particle to pass through the measurement field irradiated with laser light, and therefore the frequency variable oscillator 40a can be sufficiently controlled within such a period of time.

When a measurement device, in which the sample 12 is used, which is contained and remaining at rest in a certain container such as a cuvette and irradiated with laser light, the following measurement method may be employed.

The data processing unit 30 controls the frequency of the modulation signal so that the value of a phase delay comes close to a preset value, and calculates a fluorescence relaxation time from the phase delay and the frequency of the modulation signal at the time when the control of the frequency is settled. The data processing unit 30 also controls the signal level of the DC component and the gain to find the signal level of the DC component and the gain allowing the value of the fluorescence intensity signal to fall within a preset range at a time when controlling the frequency of the modulation signal.

According to this embodiment, the frequency of a modulation signal for modulating the intensity of laser light is adjusted so that a phase delay comes close to a preset value when a fluorescence relaxation time is calculated, thereby making the contribution of a phase delay to a fluorescence relaxation time not nonlinear but constant. Therefore, according to this embodiment, it is possible to expand the range of a fluorescence relaxation time that can be calculated with a given accuracy. For example, assuming that fluorescence is a relaxation response of a first-order lag, this embodiment allows tan θ (θ is defined as a phase delay), which is a nonlinear part, to have a substantially constant value irrespective of a fluorescence relaxation time. This makes it possible to prevent the calculation accuracy of a fluorescence relaxation time from varying due to a great difference in the contribution of tan θ between when the phase delay θ is large and when the phase delay θ is small.

Particularly, according to this embodiment, by setting the preset value to 45 degrees, the sensitivity of a phase delay to be calculated to the frequency of the modulation signal can be made high. This makes it possible to calculate a fluorescence relaxation time with high accuracy.

Further, according to this embodiment, it is possible to determine the phase delay θ with a given accuracy over a wide range by adjusting the signal levels of Re and Im components acquired from a fluorescent signal. When the signal levels of the Re and Im components are low, the Re component and the Im component may contain an error due to contamination by noise generated by the IQ mixer 42b, the low-pass filter 42c, and the AD converter 44b. If AD conversion is performed in this state, a quantization error is increased so that the error of the phase delay θ calculated using the A/D-converted Re and Im components is increased. However, according to this embodiment, the signal levels of the Re and Im components can be maintained constant by allowing a fluorescence intensity signal calculated from the Re and Im components to fall within a preset range, thereby reducing the error of the phase delay θ to a certain level or suppressing the error of the phase delay θ.

In the above description, the adjustment is performed so that both the value of a phase delay and a fluorescence intensity signal fall within their respective preset ranges, but only the determination as to whether the value of the phase delay falls within a preset range may be made without making a determination as to whether the value of the fluorescence intensity signal falls within a preset range.

The fluorescence detecting device and fluorescence detecting method according to the present invention have been described above in detail, but the present invention is not limited to the above embodiments and it should be understood that various changes and modifications may be made without departing from the scope of the present invention.

DESCRIPTION OF REFERENCE NUMERALS 10 flow cytometer
12 sample
22 laser light source unit
22a laser light source
22b, 24b, 26b lens systems
22c laser driver
24, 26 light-receiving units
24a, 26a photoelectric converters
26c shielding plate
28 control/processing unit
30 data processing unit (computer)
30a fluorescence intensity signal generation unit
30b fluorescence intensity calculation unit
30c phase delay calculation unit
30d signal control unit
30e fluorescence relaxation time calculation unit
32 tube
34 collection vessel
40 modulation signal control unit
40a frequency variable oscillator
40b power splitter
40c, 40d, 44a amplifiers
40e DC signal generator
42 frequency conversion unit
42a variable amplifier
42b IQ mixer
42c low-pass filter
42d 90 degrees phase shifter
42e, 42f mixers
44 AD conversion unit
44b AD converter

The invention claimed is:

1. A device for detecting fluorescence by processing a fluorescent signal obtained by receiving fluorescence emitted by a measurement object which is irradiated with laser light, the device comprising:
a light source unit operable to emit laser light with which a measurement object is irradiated while modulating an intensity of the laser light;
a light-receiving unit operable to output a fluorescent signal of fluorescence emitted by the measurement object irradiated with the laser light;
a light source control unit operable to generate a modulation signal including DC component for modulating the intensity of the laser light emitted from the light source unit;
a processing unit operable to calculate, from the fluorescent signal output by the light-receiving unit, a phase delay of the fluorescence emitted by the measurement object with respect to the modulation signal and calculates a fluorescence relaxation time of the fluorescence of the measurement object using the phase delay; and
a signal control unit operable to control a frequency of the modulation signal so that a value of the phase delay comes close to a preset value, and operable to adjust an intensity level of the DC component so that an intensity of the fluorescent signal is adjusted to a predetermined level.

2. The fluorescence detecting device according to claim 1, wherein
the preset value is 45 degrees.

3. The fluorescence detecting device according to claim 1, wherein
the measurement object includes a plurality of sample particles, which intermittently pass through a measurement field irradiated with the laser light one by one at a constant rate, and
the signal control unit begins to control the frequency of the modulation signal just after each of the sample particles begins to pass through the measurement field so that the value of the phase delay comes close to the preset value, and finds the frequency of the modulation signal making the value of the phase delay to be equal to the preset value before each of the sample particles passes over the measurement field irradiated with the laser light, and calculates the fluorescence relaxation time from the phase delay obtained under a condition of the found frequency and the found frequency of the modulation signal.

4. The fluorescence detecting device according to claim 1, wherein
the measurement object, contained in a container and remaining at rest, is irradiated with the laser light, and
the signal control unit controls the frequency of the modulation signal so that the value of the phase delay comes close to the preset value, and calculates the fluorescence relaxation time from the phase delay and the frequency of the modulation signal at a time when the control of the frequency is settled.

5. The fluorescence detecting device according to claim 1, further comprising
a variable amplifier amplifying the fluorescent signal output by the light-receiving unit,
the signal control unit being further operable to adjust both of a gain of the amplifier and the DC component so that the intensity of the fluorescent signal is adjusted to a predetermined level.

6. A method for detecting fluorescence by processing a fluorescent signal obtained by receiving fluorescence emitted by a measurement object which is irradiated with laser light, the method comprising the steps of:
generating a modulation signal including DC component for modulating an intensity of laser light emitted from a laser light source unit to modulate the laser light by using the modulation signal;
obtaining a fluorescent signal of fluorescence emitted from a measurement object irradiated with the laser light;
calculating, from the fluorescent signal, a phase delay of the fluorescence with respect to the modulation signal;
controlling a frequency of the modulation signal so that a value of the phase delay comes close to a preset value, and adjusting an intensity level of the DC component so that an intensity of the fluorescent signal is adjusted to a predetermined level; and calculating a fluorescence relaxation time of the fluorescence emitted by the measurement object by using the phase delay obtained under a condition of the frequency of the modulation signal at a time when the control of the frequency is settled.

7. The fluorescence detecting method according to claim 6, wherein the preset value is 45 degrees.

8. The fluorescence detecting method according to claim 6, wherein the measurement object includes a plurality of sample particles, which intermittently pass through a measurement field irradiated with the laser light one by one at a constant rate, and the frequency of the modulation signal begins to be controlled just after each of the sample particles begins to pass through the measurement field irradiated with the laser light so that the value of the phase delay comes close to the preset value, and the frequency of the modulation signal making the value of the phase delay to be equal to the preset value, is found before the sample particle passes over the measurement field irradiated with the laser light, and the fluorescence relaxation time is calculated from the phase delay obtained under a condition of the found frequency and the found frequency of the modulation signal.

9. The fluorescence detecting method according to claim 6, wherein the measurement object, contained in a container and remaining at rest, is irradiated with the laser light, and the frequency of the modulation signal is controlled so that the value of the phase delay comes close to the preset value, and the fluorescence relaxation time is calculated from the phase delay and the found frequency of the modulation signal at a time when the control of the frequency is settled.

10. The fluorescence detecting method according to claim 6, further comprising amplifying the obtained fluorescent signal before calculating the phase delay, and adjusting both of a gain of the amplifying and the DC component so that the intensity of the fluorescent signal is adjusted to a predetermined level.

* * * * *